(12) United States Patent
Bell et al.

(10) Patent No.: US 12,399,178 B2
(45) Date of Patent: *Aug. 26, 2025

(54) SPECIMEN ENRICHMENT FOR OPTICAL TOMOGRAPHY CELL ANALYSIS

(71) Applicant: VisionGate, Inc., Woodinville, WA (US)

(72) Inventors: Timothy Bell, Phoenix, AZ (US); Alan C. Nelson, Gig Harbor, WA (US); Michael G. Meyer, Phoenix, AZ (US)

(73) Assignee: VisionGate, Inc., Woodinville, WA (US)

( * ) Notice: Subject to any disclaimer, the term of this patent is extended or adjusted under 35 U.S.C. 154(b) by 174 days.

This patent is subject to a terminal disclaimer.

(21) Appl. No.: 17/898,074

(22) Filed: Aug. 29, 2022

(65) Prior Publication Data

US 2024/0068924 A1    Feb. 29, 2024

Related U.S. Application Data

(63) Continuation of application No. 16/033,064, filed on Jul. 11, 2018, now Pat. No. 11,428,692.

(51) Int. Cl.
*G01N 33/533* (2006.01)
*B01L 3/00* (2006.01)
(Continued)

(52) U.S. Cl.
CPC .. *G01N 33/57423* (2013.01); *B01L 3/502761* (2013.01); *G01N 15/1434* (2013.01);
(Continued)

(58) Field of Classification Search
CPC ........... G01N 33/57423; G01N 33/533; G01N 33/534; G01N 33/554; G01N 15/01; G01N 2015/1486
See application file for complete search history.

(56) References Cited

U.S. PATENT DOCUMENTS 6,522,775 B2    2/2003  Nelson
6,944,338 B2    9/2005  Lock et al.
(Continued)

FOREIGN PATENT DOCUMENTS

EP    0 633 462 A2    1/1995

OTHER PUBLICATIONS

Bio-Rad, "S3™ and S3e™ Cell Sorters—Instruction Manual," 2014, 132 pages.
(Continued)

*Primary Examiner* — Gailene Gabel
(74) *Attorney, Agent, or Firm* — Seed Intellectual Property Law Group LLP

(57) ABSTRACT

A method for enhancing gating performance of a cell sorter to prepare an enriched specimen for optical tomography cell analysis includes introducing a specimen into a FACS to generate 2D event data; generating a first scatterplot of the 2D data; identifying target objects; constructing a boundary within the first scatterplot to produce a first gate; counting target objects within the first gate; comparing the number of target objects within the first gate to a first predetermined value and adjusting the first gate as necessary. A boundary around a set of target objects is constructed in a second scatterplot to produce a subset second gate and target objects within the second gate are counted and the count compared to a second predetermined value. When a boundary around target objects meets specifications the first and second gates are stored in memory and used to enrich patient specimens.

14 Claims, 9 Drawing Sheets

(51) Int. Cl.

| | | |
|---|---|---|
| *G01N 15/1434* | (2024.01) | |
| *G01N 21/64* | (2006.01) | |
| *G01N 33/554* | (2006.01) | |
| *G01N 33/574* | (2006.01) | |
| *G01N 15/01* | (2024.01) | |
| *G01N 15/14* | (2006.01) | |
| *G01N 15/149* | (2024.01) | |

(52) U.S. Cl.
CPC ..... *G01N 21/6428* (2013.01); *G01N 21/6458* (2013.01); *G01N 33/533* (2013.01); *G01N 33/554* (2013.01); *B01L 2200/0652* (2013.01); *B01L 2300/0654* (2013.01); *B01L 2300/0663* (2013.01); *G01N 15/01* (2024.01); *G01N 2015/1486* (2013.01); *G01N 15/149* (2024.01); *G01N 2021/6439* (2013.01)

(56) References Cited

U.S. PATENT DOCUMENTS

| | | | |
|---|---|---|---|
| 7,738,945 | B2 | 6/2010 | Fauver et al. |
| 7,835,561 | B2 | 11/2010 | Meyer et al. |
| 7,907,765 | B2 | 3/2011 | Fauver et al. |
| 8,080,383 | B2 | 12/2011 | Lacombe et al. |
| 8,155,420 | B2 | 4/2012 | Meyer et al. |
| 8,254,023 | B2 | 8/2012 | Watson et al. |
| 8,691,164 | B2 | 4/2014 | Butler et al. |
| 9,194,868 | B2 | 11/2015 | Buzatu et al. |
| 9,285,367 | B2 | 3/2016 | Kasinrerk |
| 9,347,933 | B2 | 5/2016 | Harrison et al. |
| 9,535,000 | B2 | 1/2017 | Guo et al. |
| 11,428,692 | B2 * | 8/2022 | Sussman ............ G01N 21/6428 |
| 2014/0343897 | A1 * | 11/2014 | Trotter ................ G06V 10/457 |
| | | | 702/189 |

OTHER PUBLICATIONS

Bio-Rad Laboratories Inc., "Flow Cytometry: Basic Guide.", (2016).

Böcking et al., "Diagnosis of Bronchial Carcinoma on Sections of Paraffin-Embedded Sputum," *Acta Cytologica* 36(1): 37-47, 1992. (12 pages).

Brown et al., "Flow Cytometry: Principles and Clinical Applications in Hematology," *Clinical Chemistry* 46(8): Aug. 2000.

Duggan, "Basic Parameters Measured by a Flor Cytometer: What is Scattered Light and Absolute Fluorescence?" https://bitesizebio.com/25310/basic-parameters-measured-by-a-flow-cytometer-what-is-scattered-light-and-absolute-fluorescence/, accessed on Oct. 26, 2017.

Neumann et al., "Premalignant and Malignant Cells in Sputum From Lung Cancer Patients," *Cancer Cytopathology* 117:473-481, 2009.

Schreiber et al., "Performance Characteristics of Different Modalities for Diagnosis of Suspected Lung Cancer," *Chest* 123:115S-128S, 2003.

* cited by examiner

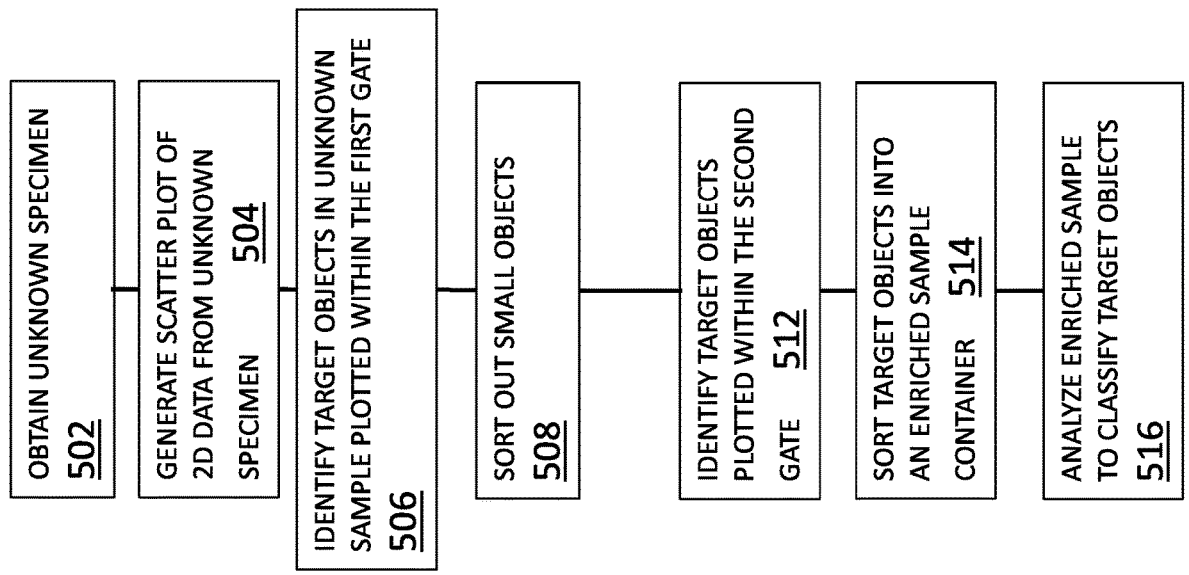

SPECIMEN ENRICHMENT FOR OPTICAL TOMOGRAPHY CELL ANALYSIS

TECHNICAL FIELD

The present invention relates to enriching specimens for use in optical computed tomography on a cellular and sub-cellular scale. More particularly, the invention relates to a system and method for gating objects and sorting the objects to prepare an enriched sample for optical computed tomography cell analysis.

BACKGROUND

Lung cancer is the second most prevalent cancer in the United States and is the most lethal. Over 31 million patients in the United States (US) are at high risk for the development of lung cancer, primarily due to age, smoking history, and pollution and other factors including radon exposure, family history of lung cancer, etc. Approximately 160,000 US patients die of lung cancer each year. At the time of this writing, lung cancer can only be cured with surgery when detected in early stages, mainly stage I and II.

In an effort to promote early lung cancer detection, advances in 3D imaging of biological cells using optical computed tomography have been developed by Nelson as disclosed, for example, in U.S. Pat. No. 6,522,775, issued Feb. 18, 2003, and entitled "Apparatus and Method for Imaging Small Objects in a Flow Stream Using Optical Tomography," the full disclosure of which is incorporated by reference. Further major developments in the field are taught in Fauver et al., U.S. Pat. No. 7,738,945, issued Jun. 15, 2010, entitled "Method and Apparatus for Pseudo-Projection Formation for Optical Tomography," (Fauver '945) and Fauver et al., U.S. Pat. No. 7,907,765, issued Mar. 15, 2011, entitled "Focal Plane Tracking for Optical Microtomography," (Fauver '765) the full disclosures of Fauver '945 and Fauver '765 are also incorporated by reference. Building on the teachings therein, an early lung cancer detection technology has been developed by VisionGate, Inc., Phoenix, AZ to provide measurement advantages that have demonstrated a great improvement in the operating characteristics of conventional morphologic cytology analyses.

Processing in such an optical computed tomography system begins with specimen collection and preparation. For diagnostic applications in lung disease, patient sputum can be collected non-invasively in a clinic or at a patient's home. The sputum is then processed to remove some of the non-diagnostic material, fixed and then stained in a clinical lab. Stained specimens are then mixed with an optical gel, and the suspension is injected into a microcapillary tube. Images of objects, such as cells, in the specimen are collected while the cells are rotated around 360-degrees relative to the image collection optics in an optical tomography system. The resultant images comprise a set of extended depth of field 2D images from differing perspectives called "pseudo-projection images." The set of pseudo-projection images can be mathematically reconstructed using backprojection and filtering techniques to yield a volumetric 3D reconstruction of a cell of interest. Having isometric or roughly equal sub-micron spatial resolution in all three dimensions is an advantage in 3D tomographic cell imaging, especially for quantitative feature measurements and image analysis.

The 3D reconstructed digital image then remains available for further analysis to enable the quantification through the measurement of sub-cellular structures or molecular probes of interest. An object such as a biological cell may be stained or labeled with at least one absorbing contrast agent and/or tagged with a molecular probe, and the measured amount and structure of this biomarker may yield important information about the disease state of the cell, including, but not limited to, various cancers such as lung, breast, prostate, cervical, stomach and pancreatic cancers, and various stages of dysplasia.

Each patient sample may include up to millions of objects that can register as events. However, only certain target cells have diagnostic value for disease, such as lung cancer. Processing all of the objects in the sample uses an excessive amount of processing resources and time. Because individual cells are analyzed for each optical tomography sample and each analyzed cell must be processed for 3D reconstruction, there is a need to enrich samples to eliminate extraneous objects and non-target cells, such as oral squamous cells (OSC) and immune cells, while processing a high percentage of target cells. Disclosed herein is a method and system for enriching sample prior to submitting it to optical tomography analysis and 3D reconstruction.

BRIEF SUMMARY OF THE DISCLOSURE

This summary is provided to introduce, in a simplified form, a selection of concepts that are further described below in the Detailed Description. This summary is not intended to identify key features of the claimed subject matter, nor is it intended to be used as an aid in determining the scope of the claimed subject matter.

Disclosed herein is a method for enhancing gating performance of a cell sorter to prepare an enriched specimen for optical tomography cell analysis that includes introducing a controlled specimen including a plurality of known objects treated with an Ab cocktail into a fluorescence-activated cell sorter (FACS) to generate a first set of 2D event data, wherein the known objects include a plurality of known target objects; generating a first scatterplot of the first set of 2D event data; locating a first set of the known target objects in the first scatterplot, wherein the known target objects each meet or exceed a target size; constructing a first gate boundary within the first scatterplot to produce a first gate around a portion of the first set; counting the known target objects within the first gate to produce a first value; comparing the first value to a first predetermined value, if the first value meets or exceeds the first predetermined value then proceeding to the next operation, otherwise, adjusting the first gate boundary and repeating until the first predetermined value is satisfied; generating a second scatterplot containing a subset of the first set of 2D event data in the first scatterplot; constructing a second gate boundary around a second set of known target objects in the second scatterplot to produce a second gate; counting the second set of known target objects within the second gate boundary to produce a second count; and comparing the second count to a second predetermined value, and if the percent of target objects within the second gate meets or exceeds a second predetermined value the first and second gate boundaries are stored in memory operation otherwise, the second boundary is adjusted until the predetermined criteria is met for the second gate.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

FIG. 5 is a process flow diagram for one example of a method for sorting unknown objects using enhanced FACS gating.

Figure 1:
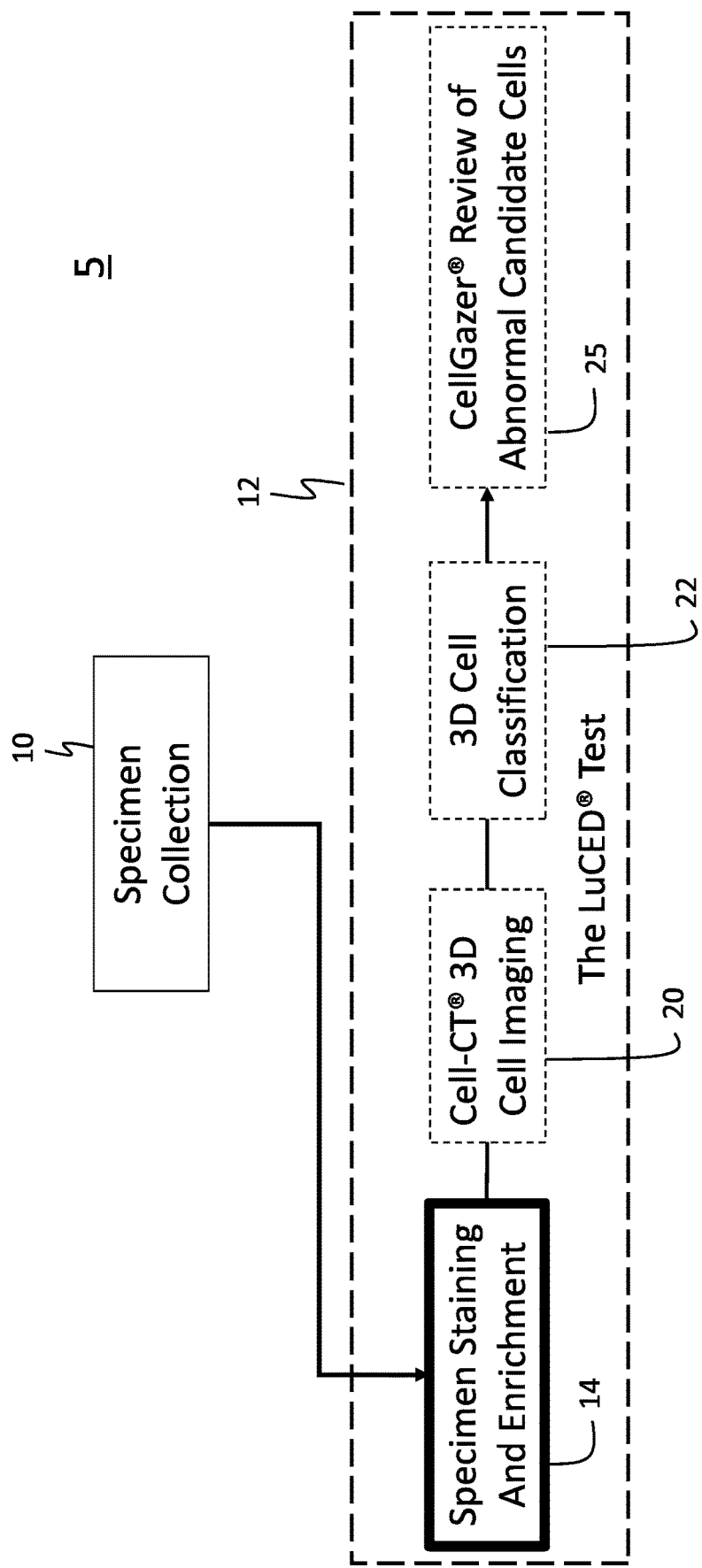
FIG. 1 schematically shows a functional overview of a lung cancer test for analysis of a sputum sample.

In the drawings, identical reference numbers call out similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not necessarily intended to convey any information regarding the actual shape of the particular elements and have been solely selected for ease of recognition in the drawings.

DETAILED DESCRIPTION OF THE PREFERRED EMBODIMENTS

The following disclosure describes a method and system for method for gating objects and sorting the objects to prepare an enriched sample for optical tomography cell analysis. Several features of methods and systems in accordance with example embodiments are set forth and described in the figures. It will be appreciated that methods and systems in accordance with other example embodiments can include additional procedures or features different than those shown in the figures. Example embodiments are described herein with respect to FACS for providing an enriched sample for an optical tomography cell imaging system. However, it will be understood that these examples are for the purpose of illustrating the principles, and that the invention is not so limited.

Definitions

Generally, as used herein, the following terms have the following meanings, unless the use in context dictates otherwise:

The use of the word "a" or "an" when used in conjunction with the term "comprising" in the claims or the specification means one or more than one, unless the context dictates otherwise. The term "about" means the stated value plus or minus the margin of error of measurement or plus or minus 10% if no method of measurement is indicated. The use of the term "or" in the claims is used to mean "and/or" unless explicitly indicated to refer to alternatives only or if the alternatives are mutually exclusive. The terms "comprise", "have", "include" and "contain" (and their variants) are open-ended linking verbs and allow the addition of other elements when used in a claim.

Reference throughout this specification to "one example" or "an example embodiment," "one example," "an example" or combinations and/or variations of these terms means that a particular feature, structure or characteristic described in connection with the example is included in at least one example of the present disclosure. Thus, the appearances of the phrases "in one example" or "in an example" in various places throughout this specification are not necessarily all referring to the same embodiment or example. Furthermore, the particular features, structures, or characteristics may be combined in any suitable manner in one or more embodiments or examples.

"Adequacy" refers to the content of the specimen and defines a limit for target cells to determine if a sufficient cellular pellet has been analyzed.

"Capillary tube" has its generally accepted meaning and is intended to include transparent microcapillary tubes and equivalent items with an inside diameter generally of 500 microns or less, but larger diameters could be used.

"Cell" means biological cell such as a human, mammal or animal cell.

"Cell-CT™ platform" refers to an optical tomography system manufactured by VisionGate, Inc. of Phoenix, AZ incorporating teachings of the Nelson and Fauver patents referenced herein above and improvements of those teachings.

"CellGazer" refers to a software-based utility underdevelopment by VisionGate, Inc. for fostering review of 2D and 3D images of cells rendered by the Cell-CT platform. The result of cell review is a detailed differential diagnosis of the cell type that then determines the final result of a case processed, for example by the LuCED test.

"Chimeric antigen receptors (CARs)" as used herein mean Artificial T cell receptors (also known as chimeric T cell receptors, or chimeric immunoreceptors) are engineered receptors, which graft an arbitrary specificity onto an immune effector cell.

"CIS" as used herein has its generally accepted meaning of Carcinoma in situ, also known as in situ neoplasm.

"Depth of field" is the length along the optical axis within which the focal plane may be shifted before an unacceptable image blur for a specified feature is produced.

"Enrichment" refers to the process of extracting target cells from a raw specimen. The process yields an enriched pellet whose cells can then be more efficiently imaged on the Cell-CT system.

"Gates" as used herein refers to a defined region used of the FACS signal(s) or parameter(s) to isolate a specific group of events, for example cytometric events, from a large set of data. Gates can be customized by using Boolean logic to link multiple gates together.

"LuCED® test" refers to an early lung cancer detection test employing the Cell-CT® platform as developed by VisionGate, Inc. of Phoenix, AZ incorporating the teachings of the Nelson and Fauver patents referenced hereinabove and improvements of those teachings.

"The LuCE0® process" refers to the mechanism of 3D cell reconstruction, classification to find abnormal cells, and pathology confirmation.

"Object" means an individual cell, human cell, mammal cell, item, thing or other entity.

"Pseudo-projection" includes a single image representing a sampled volume of extent larger than the native depth of field of the optics where pseudo-projection image thus formed include an integration of a range of focal plane images from a fixed "Regions" as used here in as its generally accepted meaning of shapes or objects that are drawn around a population of interest on one and 2 parameter plots.

"ROG" has its generally accepted meaning of Receiver Operator Characteristic.

"Sample" means a finished cellular preparation that is ready for analysis, including all or part of an aliquot or specimen.

"Specimen" means a complete product obtained from a single test or procedure from an individual patient (e.g., sputum submitted for analysis, a biopsy, or a nasal swab). A specimen may be composed of one or more objects. The result of the specimen diagnosis becomes part of the case diagnosis.

"Subject" as used herein means a human patient.

"Target Cell" refers to a cell from a specimen whose characterization or enumeration is especially desired. For example, in the LuCE0 test, the target cells are the normal bronchial epithelial cells. A minimum number of these must be enumerated during the test in order for a specimen to be considered as adequate for analysis.

"Threshold" as used in the context of image processing includes a decision boundary value for any measurable characteristic of a feature. Thresholds may be predetermined or set according to instrument specifications, acceptable error rates, statistics, or other criteria according to accepted pattern recognition principles.

"Voxel" as used in the context of image processing is a volume element on a 3D grid.

Overview

Referring to FIG. 1, a functional overview of a lung dysplasia and cancer test system for analysis of a sputum sample is schematically shown. The test system 5 includes apparatus and methods for sputum specimen collection 10 followed by a test for early lung cancer detection 12 such as, for example, the LuCED® test. The early lung cancer test 12 further includes an apparatus and methods for specimen staining and enrichment 14, 3D cell imaging 20, 3D cell classification 22 and clinician review of abnormal candidate cells 25.

Sputum collection is typically done through spontaneous coughs in the patient's home or through induction in a clinic. Sputum is processed to remove contaminants and non-bronchial epithelial cells as, for example, by de-bulking the white cells and oral squamous cells (OSC). The specimen is further enriched with FACS gating techniques as described hereinbelow. The enriched specimen is processed on the Cell-CT™ platform that images cells digitally in true 3D with isometric, sub-micron resolution as disclosed, for example in Nelson and Fauver referenced above. The biosignatures associated with cancer are measured on the 3D cell images and combined into a score that is used to identify those few cells that have cancer characteristics. These cells are then optionally displayed for manual cytologist review using a review station such as a CellGazer™ review station as being developed by VisionGate, Inc., Phoenix, AZ. The review station provides visual displays allowing a cytologist to view cell images in 2D and 3D to establish a definitive normal or abnormal status for specific cell candidates. Three-dimensional (3D) cell classification 22 may be carried out using techniques as disclosed herein below.

The cell imaging system 20 includes a process implemented through computer software executed, for example, by a personal computer interfacing with opto-mechanical devices to correct for motion arising during image capture. Most cell images emerge from filtered back-projection in a well-reconstructed way. A software computer algorithm identifies cells that were poorly reconstructed so they can be rejected from further processing. One example of a method for detecting poor quality reconstructions is taught by Meyer et al. in U.S. Pat. No. 8,155,420, issued Apr. 10, 2012 and entitled "System and Method for Detecting Poor Quality in 3D Reconstructions," the disclosure of which is incorporated herein by reference.

Earlier attempts at the development of a lung cancer-screening program were based on sputum cytology which showed an insufficient sensitivity to disease detection by human eye (about 60% on average) but with very good specificity (Schreiber and McCrory (2003) Chest 123 (1 Supplement): 115). This experience led some to conclude that sputum is not valuable for detection of lung cancer. A careful analysis involving sputum embedded in paraffin blocks (Böcking A, Biesterfeld S, Chatelain R, Gien-Gerlach G, Esser E., Diagnosis of bronchial carcinoma on sections of paraffin-embedded sputum. Sensitivity and specificity of an alternative to routine cytology. Acta Cytol. 1992; 36(1):37-47) showed that a typical sputum specimen actually contains abnormal cells in 86% or more of cancer patients. Collection by morning coughs over three successive days yielded optimal results. A further analysis showed that abnormal cells are present in sputum stratified by all relevant clinical factors, including tumor histologic type, size, stage and location (Neumann T, Meyer M, Patten F, Johnson F, Erozan Y, Frable J, et al. Premalignant and Malignant Cells in Sputum from Lung Cancer Patients. Cancer Cytopathology, 2009; 117(6):473-481). Based on these specimen characteristics, the presently disclosed lung cancer detection test employs spontaneous cough sputum. Initial evaluations have shown satisfactory results using sputum fixation by either Cytolyt (Hologic, Marlborough, MA) or the well-known Saccomanno's method. The question of specimen adequacy is also important for sputum cytology. Attempts at increasing the volume of the sputum expectorate have met with varied success. Sputum induction increases production of phlegm to help achieve an overall adequate sample.

Lung Cancer is a very heterogeneous type of cancer. The three main subtypes are SCLC (small cell lung cancer), AC (adenocarcinoma) and SOC (squamous cell carcinoma).

All epithelial tissues, both healthy and malignant, express cytokeratins (CK): cytoplasmic proteins that form the intermediate filament cytoskeleton within the epithelial cell. The CK family consists of 19 different polypeptides, which have been numbered 1 through 19. These CK appear to be characteristic for certain types of epithelial differentiation. It was reported that in ACs of the lung high levels of CKs 4 (in some), 7, 8, 18, and 19 are detected; in SCLC CKs 8, 18 and 19 are found; in SOC CKs 4, 7, 8, 10, 13, 18 and 19 are found and in NSCC CK 19 are detected. Therefore, it is important to simultaneously target at least CKs 4, 7, 8, 10, 13, 18 and 19 to be able to detect such cells in the sputum.

To enable detection of CKs 4, 7, 8, 10, 13, 18 and 19, prior to running the FACS enrichment method described herein on a sputum specimen, the sputum specimen was treated with the mucolytic agent dithiothreitol (OTT) (Fisher Scientific, Waltham, MA). In one example, a specimen was filtered through a 100 μm nylon net, the cells pelleted by centrifugation and resuspended in 15% dimethyl sulfoxide (DMSO) (Fisher Scientific, Waltham, MA) in Phosphate Buffered Saline (PBS) and kept at −80° C. In another example, for longer term storage, the specimen after filtration and centrifugation was resuspended in Fixcyt fixative (50% ethanol/13 mM polyethylene glycol 1500 MW) and kept at −20° C. After filtration, an aliquot containing a cell pellet of up to 100 μL of the preserved specimen was removed for lung cancer detection test analysis. The sputum cells in the specimens were stained with hematoxylin (Electron Microscopy Sciences, Hatfield, PA) for downstream lung cancer detection test imaging.

Cells were then treated with an antibody (Ab) cocktail containing fluorescent conjugates chosen to both enrich for bronchial epithelial cells and to deplete contaminating inflammatory cells (neutrophils and macrophages). In one example, after an analysis of existing commercial anti-cytokeratin antibodies, two flow cytometry-ready CK antibodies were combined into an Ab cocktail including: 1) Pan Keratin (C11) Mouse mAb (Alexa Fluor 488 conjugate) available from Cell Signaling Technology that binds human CKs 4, 5, 6, 8, 10, 13 and 18; and 2) Anti-Cytokeratin (CK3-6H5) antibody coupled to FITC (Miltenyi Biotec) that targets CKs from simple epithelia, such as 7 (it is believed to cross-block Ab specific for human CK 7 and 8), 8, 18 and 19. Fluorescence signals of both Alexa Fluor 488 and FITC dyes that are coupled to the antibodies can be excited with a 488 nm laser line. Normal columnar cells of lung express CKs 7, 8, 13, 19, basal cells express CK17. Different CKs (1, 5, 10) are also expressed in oral squamous cells (OSC), which can reduce the enrichment of target cells since C11 Ab targets CKs 5 and 10, and so, there is an overlap between the target cell population and OSC. In addition, CKs 1, 5, 6, 8, 10, 14, 18 and 19 are expressed in squamous cell carcinomas.

It was noted that, the Ab cocktail described above targets a wide variety of CKs covering most important CKs reported in literature for various forms of lung cancer but there is also a fraction of normal OSC whose expression of these markers will vary from sample to sample and will likely be included in the enriched fraction.

As will be described in more detail below, for FACS enrichment an FSC/SSC primary gate R1 was constructed to exclude debris. Subsequently, a cytokeratin-high (High FITC) and medium to low SSC secondary gate R2 was constructed. The population of cells in this secondary gate were the enriched target bronchial epithelial cells sorted for a more efficient and downstream lung cancer detection test analysis using an optical tomography system such as the Cell-CT™ optical tomography platform. The R2 gate was also constructed such that it excluded large oral squamous cells and captured >95% of anti-cytokeratin cocktail stained A549 adenocarcinoma and SW900 squamous cell carcinoma cell lines.

Examples of Sputum Enrichment and Preparation

Figure 2:
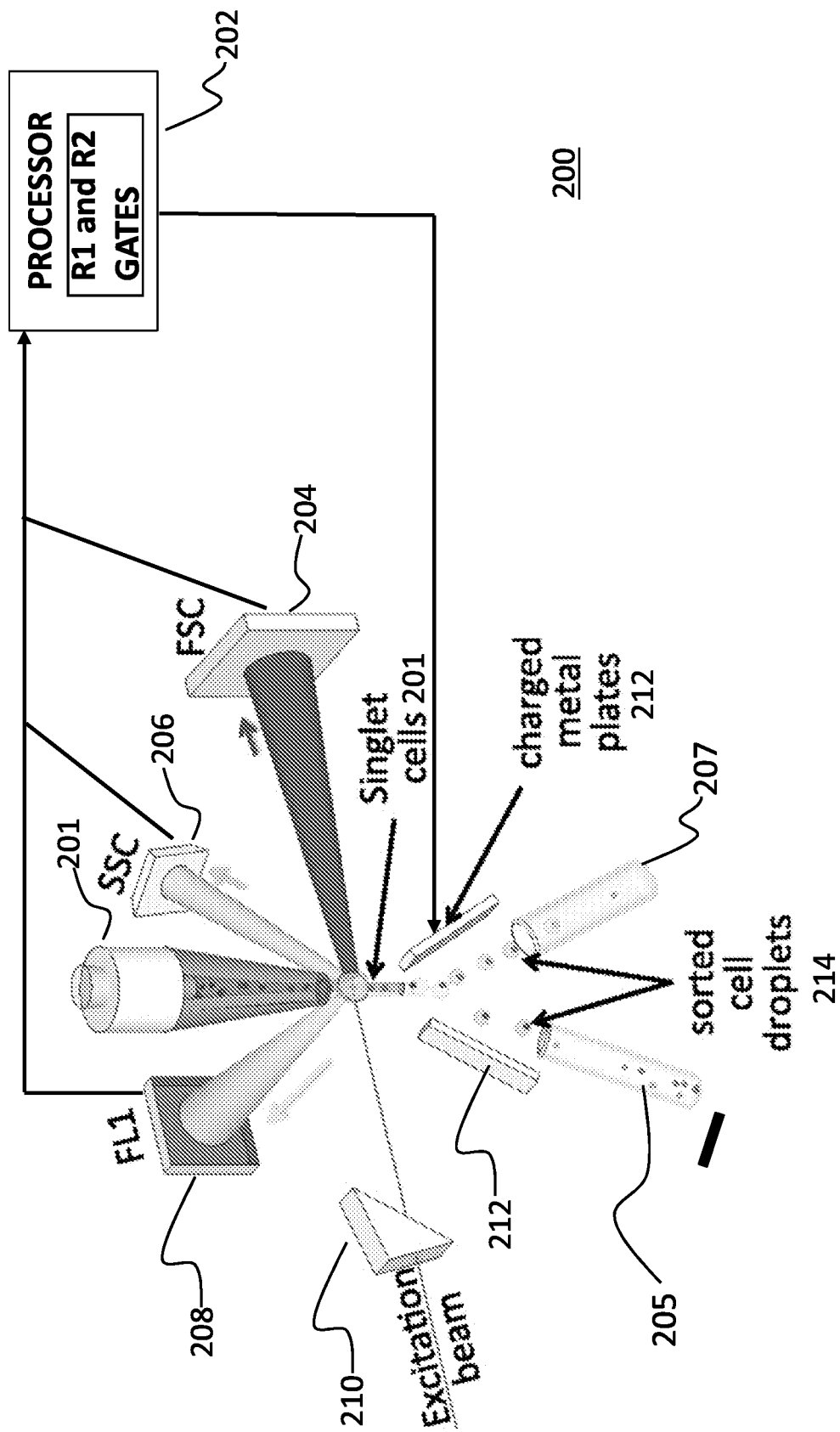
FIG. 2 schematically shows an example of a fluorescent activated cell sorter (FACS) including specimen enrichment gating.

Referring now to FIG. 2, an example of a fluorescent activated cell sorter (FACS) including specimen enrichment gating is schematically shown. A FACS 200 includes a nozzle 201, an excitation beam 210, a pair of charged metal plates 212 and at least one target object container 205. A forward scatter sensor (FSC) 204 is aligned to receive light scattering in a forward direction from around an object illuminated by the excitation beam. A side scatter sensor (SSC) 206 is aligned to receive light scattered at an oblique angle from an object illuminated by the excitation beam. A fluorescent sensor (FL1) 208 is aligned, typically at 90° from the forward direction of the excitation beam, for sensing fluorescent intensity from light emitted at the alignment angle from an illuminated object.

The FL1, SSC, and FSC sensors are coupled to a processor 202 to transmit electronic signals proportional to the intensity of the light received by the sensors. The processor may include interactive gates, adjustable by an operator. Electronic signals from the gates are used to control the charged metal plates 212. As an object is interrogated by the excitation beam by flowing through the beam, signals from the sensors can be compared and plotted for the object in real time. The plotted signals are identified as falling into the gated regions or outside of the gated regions, as will be explained in detail further below. Objects falling outside of the gated regions will be impressed with a charge of a first value in objects falling within the gated regions will be impressed with the charge of a second value. Application of the gate control signals causes the selected charges to be impressed upon singlet cells 201 flowing out of the nozzle through the excitation beam. In this way, objects meeting the criteria of both gates R1 and R2 are sorted into the target object container 205. Objects of no interest may be routed to another container 207.

The design and use of the systems and methods disclosed herein for enrichment of target objects specific to diseases such as lung cancer, for example, are new and have been developed for the first time by the inventors herein. FACS systems are available and may be obtained from, for example, Bio-Rad Laboratories, Inc. at various locations throughout the world, including the US. In some examples, the specimen may include objects from sputum, blood, urine, cervical scrapes, bowel scrapes, skin scrapes, plural effusion and liquid biopsy samples. Typically, excitation beams comprise laser beams having wavelengths in the range of about 405 nm to about 700 nm, more preferably in the range of about 488 nm to about 550 nm depending on the fluorescent markers being used to stain objects. Typically, fluorescent detector channels may range from about 500 nm to about 660 nm. In the examples described herein the fluorescent detector FL1 is selected to be sensitive to 500-600 nm wavelengths.

In certain examples target cells include abnormal squamous cells, adenocarcinoma cells, bronchioloalveolar carcinoma cells, abnormal neuroendocrine cells, small cell carcinoma cells, large cell carcinoma cells, lung columnar cells, tumor cells, neoplastic cells and bronchioloalveolar carcinoma cells and other cells and objects found in sputum.

In certain other examples, some cells, such as squamous cells, may be excluded because they will not be objects of interest.

Figure 3:
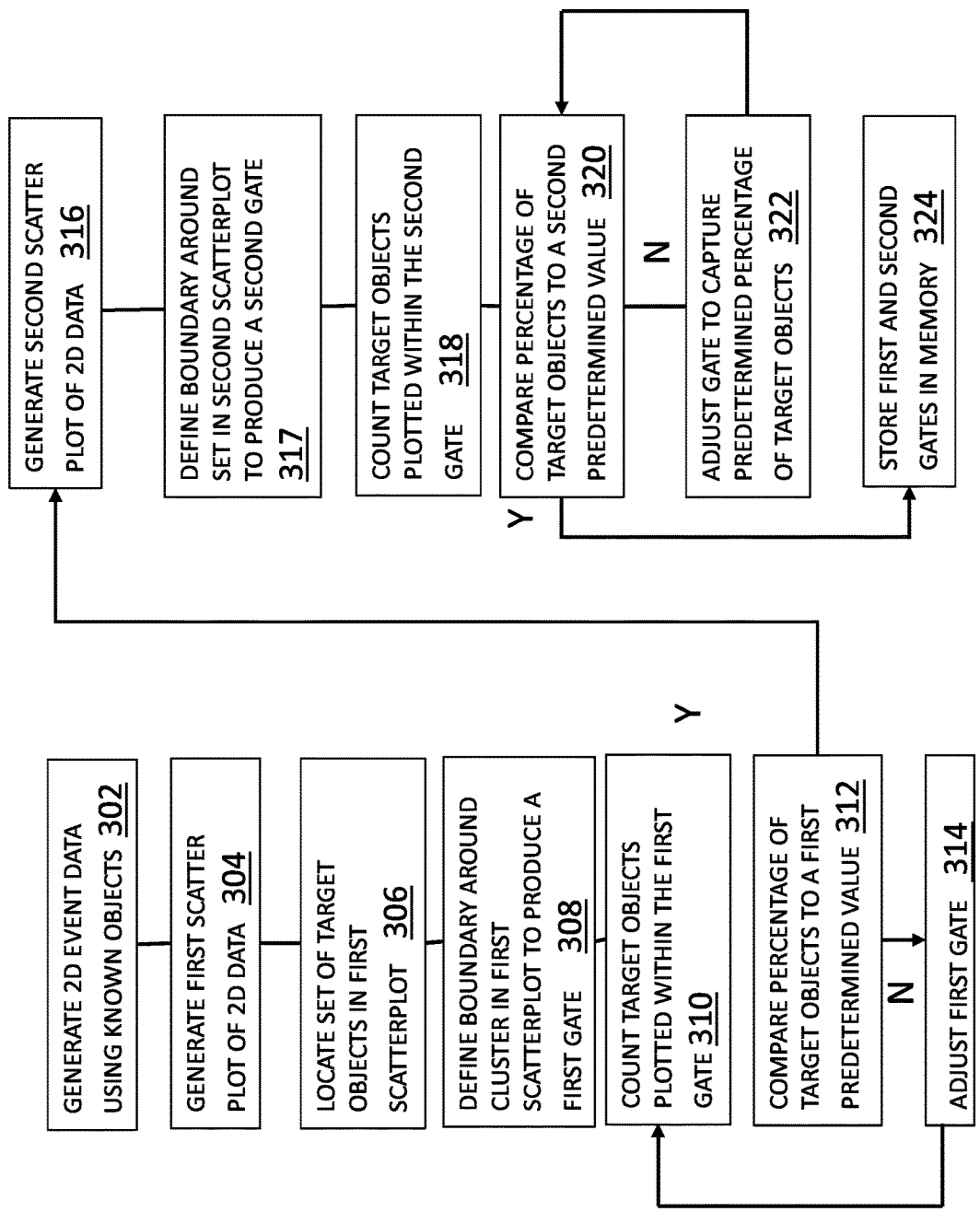
FIG. 3 is a process flow diagram for one example of a method for optimizing a cell sorter in order to generate gates for target objects from known objects.

Referring now to FIG. 3, a process flow diagram for one example of a method for optimizing improving operation of the primary and secondary gates for discriminating target objects from known objects is schematically shown. A plurality of known objects, such as biological cells from a cell line and/or calibration beads, may be introduced into the FACS to generate 2D event data at operation 302. A first scatterplot data, such as a scatterplot of SSC values versus FSC values for a plurality of known objects may be generated at operation 304. Target objects, here the known objects, in the first scatterplot may be identified, as by an operator, electrical circuitry or software logic at operation 306. Having located and identified the region of target objects, a boundary is constructed within the first scatterplot to produce a first gate at operation 308. Target objects within the first gate are then counted at operation 310. At operation 312 the percentage of target objects within the first gate are compared to a predetermined value. If the percent of target objects within the first gate meets or exceeds the predetermined value a boundary around a target cluster in a second scatterplot is generated at operation 316. Otherwise, the first gate is adjusted at operation 314 and operations 310 and 312 are repeated until the predetermined criteria is met for the first gate.

At operation 317 a boundary around a cluster in a second scatterplot is generated to produce a second gate. The second scatterplot is a subset or "daughter" gate of the first "mother" gate. That is to say that objects falling within the first gate R1 are re-plotted as a second scatterplot of SSC values versus FL1 values for each object. Having located and identified the region of target objects within the second scatterplot, a boundary is constructed within the second scatterplot to produce a second gate at operation 317. Target objects within the second gate are then counted at operation 318. At operation 320 the percentage of target objects within the second gate is compared to a second predetermined value. If the percent of target objects within the second gate meets or exceeds the second predetermined value a boundary around a target cluster the first and second gates are stored in memory operation 324 and this first stage of gate optimizing is complete. Otherwise, the second gate is adjusted at operation 322 and operations 320 and 322 are repeated until the predetermined criteria is met for the second gate.

While quality control criteria may vary, the first predetermined value may advantageously be set at a minimum of about 80%, 85% or 90% or higher. The second predetermined value may advantageously be set at a minimum of 80%, 85% or 90% or higher of events detected within the R2 gate.

In one example, a method for enhancing gating performance of a cell sorter to prepare an enriched specimen for optical tomography cell analysis includes introducing a controlled specimen including a plurality of known objects treated with an Ab cocktail into a fluorescence-activated cell sorter (FACS) to generate a first set of 2D event data, wherein the known objects include a plurality of known target objects; generating a first scatterplot of the first set of 2D event data; locating a first set of the known target objects in the first scatterplot, wherein the known target objects each meet or exceed a target size; constructing a first gate boundary within the first scatterplot to produce a first gate around a portion of the first set; counting the known target objects within the first gate to produce a first value; comparing the first value to a first predetermined value, if the first value meets or exceeds the first predetermined value then proceeding to the next operation, otherwise, adjusting the first gate boundary and repeating until the first predetermined value is satisfied; generating a second scatterplot containing a subset of the first set of 2D event data in the first scatterplot; constructing a second gate boundary around a second set of known target objects in the second scatterplot to produce a second gate; counting the second set of known target objects within the second gate boundary to produce a second count; and comparing the second count to a second predetermined value, and if the percent of target objects within the second gate meets or exceeds a second predetermined value the first and second gate boundaries are stored in memory operation otherwise, the second boundary is adjusted until the predetermined criteria is met for the second gate.

In one example, the first predetermined value is set at a minimum of at least 80%, at least 85% or at least 90% or higher of the known target objects.

In another example, the second predetermined value is set at a minimum of at least 80%, at least 85% or at least 90% or higher of the known target objects.

In another example, the known target objects comprise CK-FITC/CK-Alexa 488 stained A549 cells.

In one useful example, the first scatterplot is a plot of the 2D event data including side scatter area vs. forward scatter sensor area and the second scatterplot is a plot of the 2D event data including side scatter area vs. fluorescence area.

Figure 4:
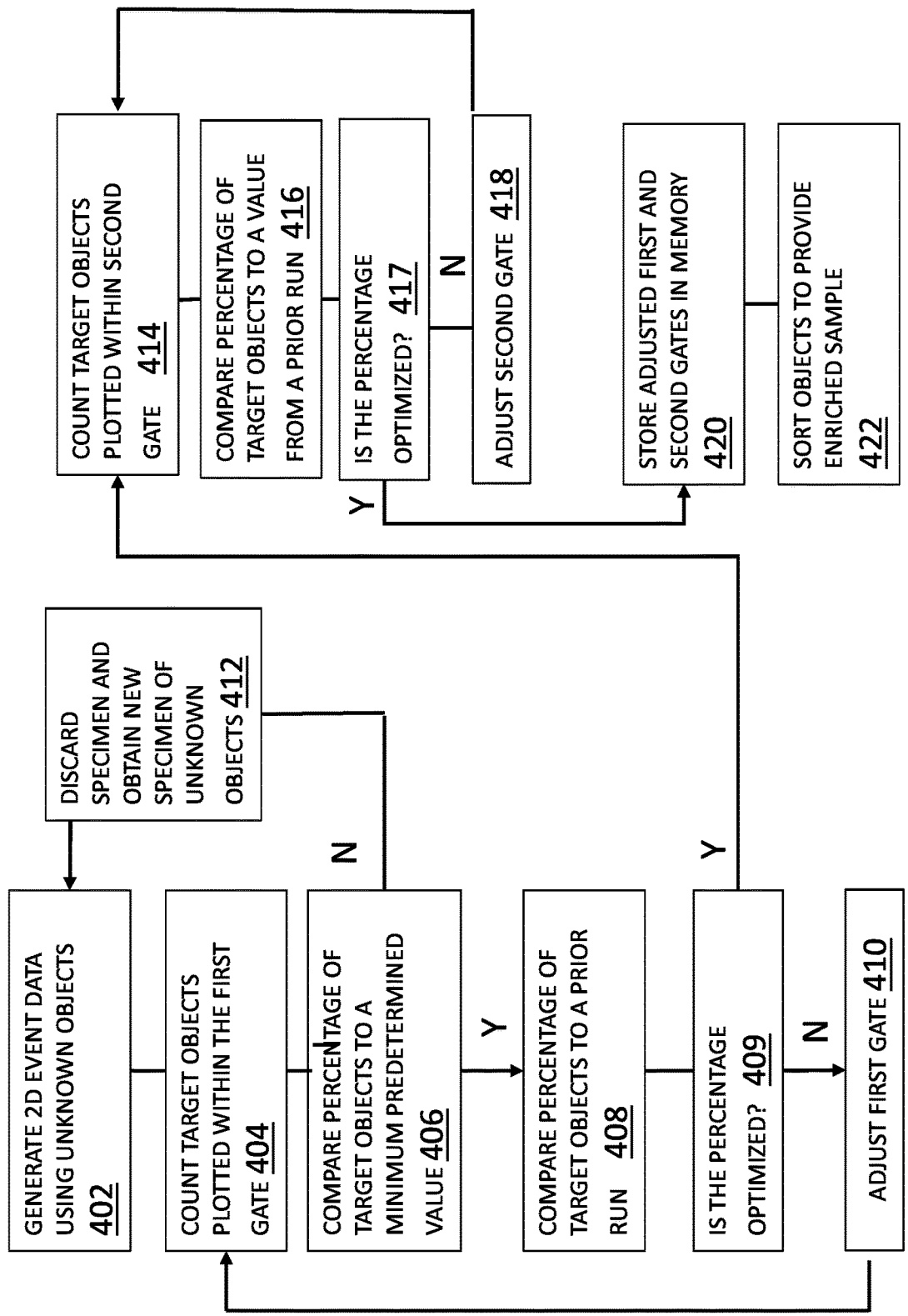
FIG. 4 is a process flow diagram for one example of a method for optimizing a cell sorter operation in order to construct appropriate gates for target objects from unknown objects.

Referring now to FIG. 4, a process flow diagram for one example of a method for optimizing a cell sorter in order to construct useful gates for target objects from unknown objects is shown. For further optimization of the R1 and R2 gates, specimens of unknown objects, such as biological cells from a patient sample, may be introduced into the FACS to generate 2D event data at operation 402. A first scatterplot of the 2D data, such as a scatterplot of SSC values versus FSC values for a plurality of patient-derived objects are subjected to the first gate R1 at operation 404 for identification of patient-derived target objects. At operation 406 the percentage of patient-derived target objects within the first gate are compared to a predetermined minimum value. If the predetermined minimum value is not detected, the specimen is discarded and a new specimen of unknown patient-derived objects is obtained at operation 412 and the process restarts at operation 402. If the percent of patient-derived target objects within the first gate meets or exceeds the predetermined minimum value, the percentage of patient-derived target objects is compared to the prior run at operation 408. When the percentage of target objects is optimized as determined at operation 409, the operation proceeds to count target objects plotted within the second gate at operation 414. Otherwise, the first gate is adjusted at operation 410 and operations 404 through 409 are repeated as necessary until the predetermined criteria is met for the first gate. As used here, optimization results when the number of patient-derived target objects counted reach of maximum number within a preselected or otherwise acceptable tolerance. Many specimens can be run to further optimize the R1 and R2 gates, for examples tens, hundreds, thousands or more specimens may be sorted to optimize the gates.

Patient-derived target objects are then counted within the second gate at operation 414. At operation 416 the percentage of target objects within second gate are compared to a prior run through the second gate. If the percent of patient-derived target objects within the second gate meets optimization criteria 417, the first and second gates are stored in memory at operation 420 and this second stage of the gate optimizing is complete. Otherwise, the second gate is adjusted at operation 418 and operations 414 through 418 are repeated as necessary until the predetermined criteria is met for the second gate. The stored first and second gates may then be used for sorting target objects in order to provide an enriched sample at operation 422.

FIG. 5 is a process flow diagram for one example of a method for sorting objects. Having established optimized gates R1 and R2, the gates can now be applied against other unknown specimens in order to provide an enriched sample for subsequent processing by an optical tomography system. An unknown specimen is obtained at operation 502 and a scatterplot of 2D data from the unknown specimen is generated at operation 504. Target objects from the unknown specimen plotted within the first gate R1 are identified. Smaller objects appearing outside of the R1 gate are sorted out into waste or another container for non-target objects at operation 508. Other objects are interrogated with respect to the second gate R2 at operation 510. Note that the signals for both gates R1 and R2 are collected simultaneously, and thus the object selection based on the gates takes place substantially contemporaneously.

Target objects plotted within the second gate R2 are identified at operation 512. The target objects are then sorted into an enriched sample container at operation 514 and, when the specimen is depleted, the enriched sample container is provided for further analysis at operation 516.

Once the first and second gates have been established as described hereinabove, an unknown specimen with patient-derived cells can be sorted according to the following operations including the patient specimen into the FACS to generate unknown object 2D event data, wherein the patient specimen includes a plurality of patient-derived target objects; overlaying the first gate over the unknown object 2D event data and counting a first number of the plurality of patient-derived target objects within the first gate; if not the first iteration, then comparing the count of the plurality of patient-derived target objects to a prior iteration; if the count of patient-derived target objects is optimized, the operation proceeds to count target objects plotted within the second gate, otherwise, the first gate is adjusted and operations repeated until the number of patient-derived target objects counted within the first gate reach a maximum number within a preselected tolerance; overlaying the second gate over patient-derived target objects counted in the first gate unknown object 2D event data and counting a second number of patient-derived target objects; if not the first iteration for the second gate, then comparing the second number of patient-derived target objects to a prior iteration count; if, after a plurality of iterations, the second number is optimized, the operation proceeds to the next operation, otherwise, the second gate is adjusted and operations are repeated as necessary until the second number reaches a maximum number within a preselected tolerance; storing the first and second gates in memory; and sorting patient-derived target objects bounded within both the first and second gates to produce an enriched sample.

In one example, the Ab cocktail comprises Pan Keratin (C11) Mouse mAb and Anti-Cytokeratin (CK3-6H5) antibody coupled to FITC.

In another example the first and second gates are stored in memory and using the stored first and second gates for sorting cells from a patient specimen to provide an enriched specimen.

In another example, the specimen is a biological specimen obtained from a patient selected from the group consisting of sputum, blood, a buccal swab, a venipuncture, plasma, skin, DNA, organ tissue, esophageal cells and a nasal swab.

In another example, the target objects comprise biological cells from the group consisting of lung cells, esophageal cells, cancer cells, dysplastic cells, normal cells, epithelial cells and combinations thereof.

In another example, the cancer cells comprise lung cancer cells.

In another example, the epithelial cells comprise lung cells.

In another example, the human-derived target cells comprise lung cells from a sputum specimen.

Figures 6A, 6B:
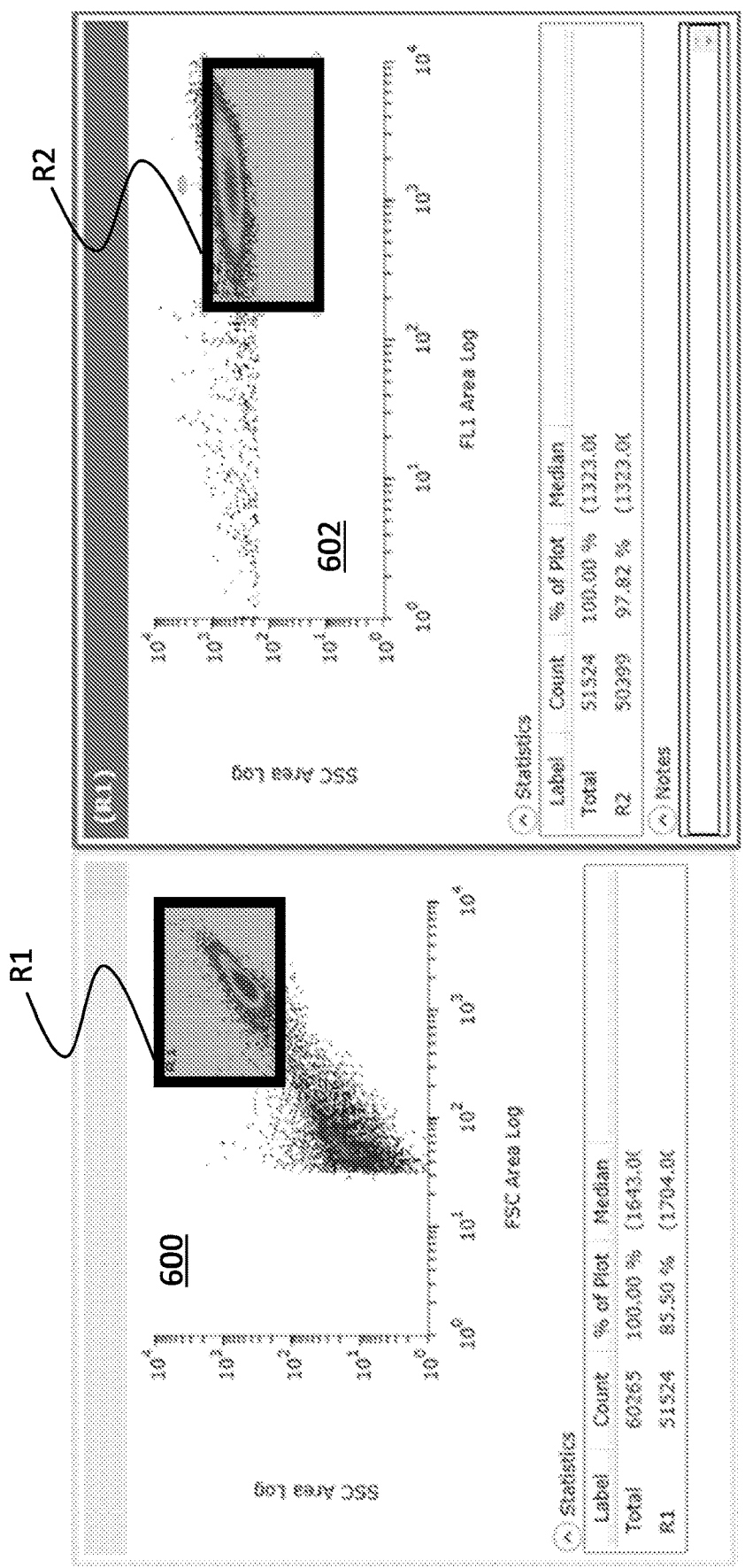
FIG. 6A is a computer screenshot that graphically shows an side-scattered (SSC) vs. front-scattered (FSC) signal scatterplot for detected objects in a sample of hematoxylin-stained A549 adenocarcinoma cells stained with a mixture of several fluorescently labeled pan-cytokeratin antibodies.
FIG. 6B is a computer screenshot that graphically shows an SSC vs. fluorescence (FL1) signal scatterplot of detected objects captured in the SSC/FSC R1 gate shown in FIG. 5A.

Referring now to FIG. 6A, a computer screenshot of an example of an FACS sort analysis of known objects graphically shows an SSC vs. FSC scatterplot for known objects. During optimizing gate generation, scatterplot 600 plots SSC area log versus FSC area log for a total of 60265 events from a FACS run where 85.50% or 51524 events have values within gate R1. Objects plotted are known objects from a cell line. Events correspond to objects. Thus, objects falling outside of gate R1 are sorted out as too small for meeting the criteria of size for objects of interest, such as biological cells or debris.

Referring now to FIG. 6B, a computer screenshot of an example of an FACS sort analysis of known objects graphically shows an SSC vs. FL1 scatterplot for known objects. During gate optimization, scatterplot 602 plots SSC area log versus FL1 area log for a total of FL1 events residing in R1 for the same FACS run of known objects from a cell line. Events having values within gate R2 number 50399 or 97.82% of events residing in the window defined by the R1 gate. Thus, objects falling outside of gate R2 are sorted out as objects of no interest, while the remaining objects, most of which will be such as biological cells of interest, are sorted into the enriched object container.

Now jointly referencing FIG. 6A and FIG. 6B, in one example the known objects include A549 lung adenocarcinoma cells cultured, FCT-fixed, Gill and CK-antibody stained according to known practices using stain including Gill hematoxylin. In order to prevent staining the cells too darkly, the Gill hematoxylin was diluted 1:1 with dH2O. Beads were also used straight or diluted in PBS as indicated below. Samples were analyzed on cell sorter following the Bio-Rad Operation SOP, using the optimized R1 forward scatter/side scatter and R2 FL1 (detects FITC/Alexa 488 nm fluorescence) gates. Several thousand events were acquired for each sample and the percent events within the R1 and R2 gates recorded.

Shown is a typical quality control (QC) evaluation display of the set gates using CK-FITC/CK-Alexa 488 stained A549 cells. The R1 gate, capturing the cell population from debris and noise, acquired ~85% of the total signal. The R2 gate, which isolates the CK-FITC/CK-Alexa 488 positive cells that are within the R1 gate and is the one that is used for LuCED 1.5 enrichment of sputum, captured >97% of the A549 cells. This result would pass the QC requirement for the set gates.

Figures 7A, 7B:
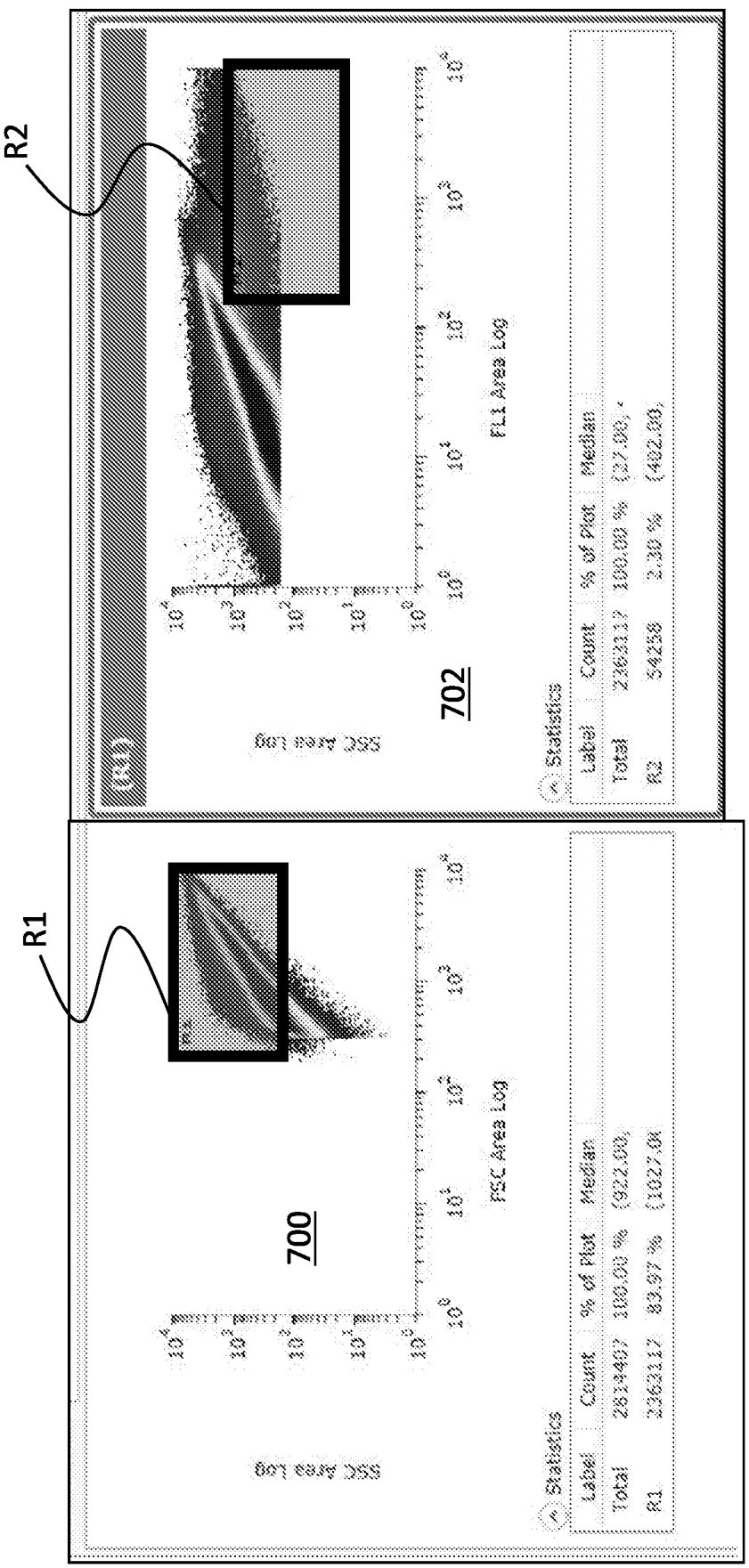
FIG. 7A is a computer screenshot that graphically shows an example of a SSC vs. FSC scatterplot of detected objects in an example of a hematoxylin-stained patient sputum sample stained with a mixture of several fluorescently labeled pan-cytokeratin antibodies.
FIG. 7B is a computer screenshot that graphically shows an example of a SSC vs. FL1 scatterplot of detected objects captured in the SSC/FSC R1 gate shown in FIG. 7A.

Referring now to FIG. 7A, a computer screenshot graphically shows an SSC vs. FSC scatterplot for an example of patient sample objects. Scatterplot 700 plots SSC area log versus FSC area log for a total of 2814407 events from a FACS run where 83.9% or 2363117 events have values within gate R1. Objects plotted are unknown objects from a sputum specimen. Events correspond to objects. Thus, objects falling outside of gate R1 are sorted out as too small for meeting the criteria of size for objects of interest, such as biological cells.

Referring now to FIG. 713, a computer screenshot graphically shows an SSC vs. FL1 scatterplot for an example of patient sample objects. Scatterplot 702 plots SSC area log versus FL1 area log for a total of FL1 events residing in the window defined by the R1 gate for the same FACS run of known objects from a cell line. Events having values within gate R2 number 54258 or 2.30% of events meeting the R1 gate criteria. Thus, objects falling outside of gate R2 are sorted out as objects of no interest, while the remaining objects, most of which will be such as biological cells of interest, are sorted into the enriched object container.

Figures 8A, 8B:
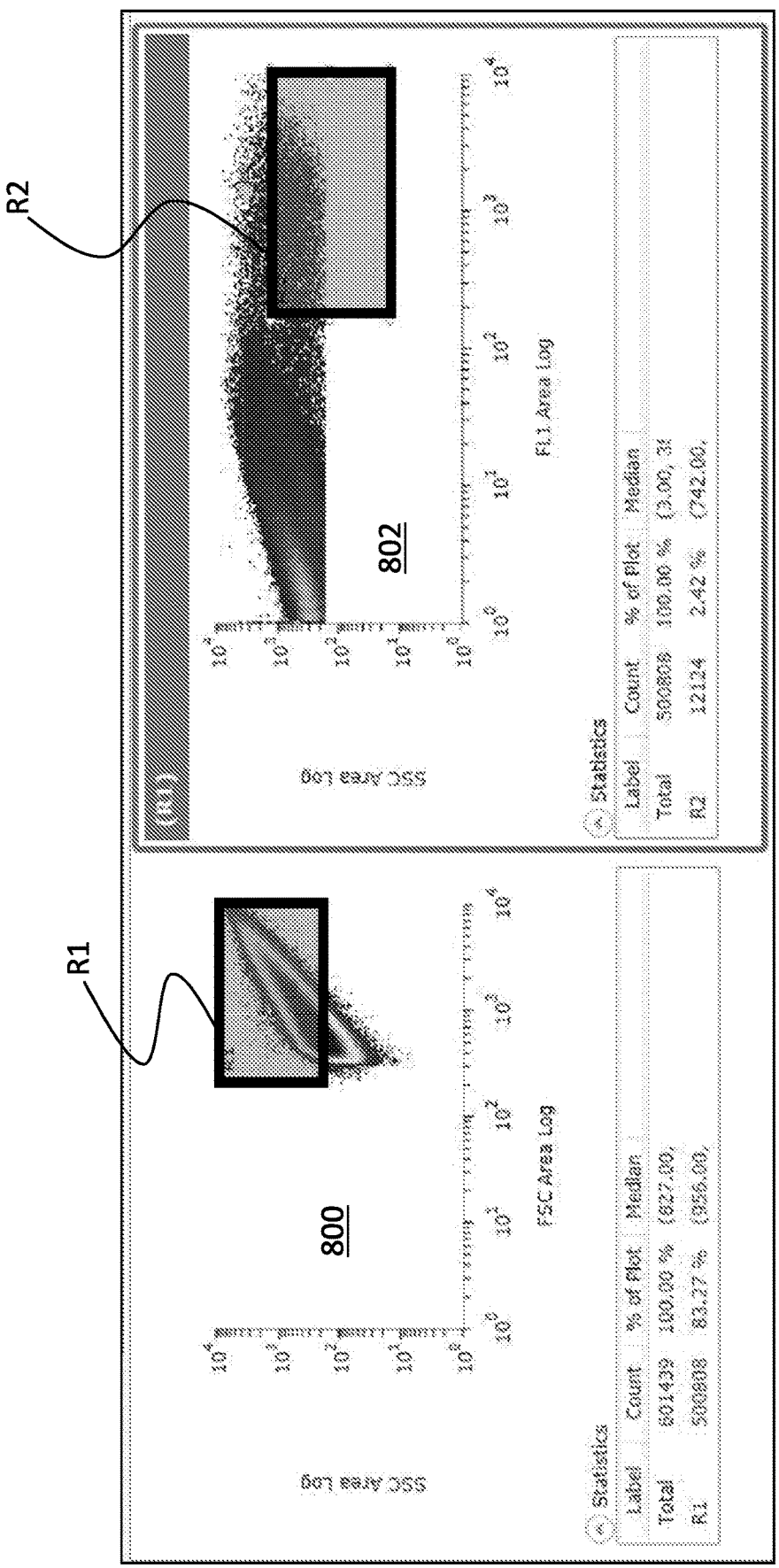
FIG. 8A is a computer screenshot that graphically shows an example of a SSC vs. FSC scatterplot for a second example of patient sample objects.
FIG. 8B is a computer screenshot that graphically shows an SSC vs. FL1 scatterplot for a second example of patient sample objects.

Referring now to FIG. 8A, a computer screenshot graphically shows an SSC vs. FSC scatterplot for an example of patient sample objects. Scatterplot 800 plots SSC area log versus FSC area log for a total of 601439 events from a FACS run where 83.27% or 500808 events have values within gate R1. Objects plotted are unknown objects from a sputum specimen. Events correspond to objects. Thus, objects falling outside of gate R1 are sorted out as too small for meeting the criteria of size for objects of interest, such as biological cells.

Referring now to FIG. 813, a computer screenshot graphically shows an SSC vs. FL1 scatterplot for an example of patient sample objects. Scatterplot 702 plots SSC area log versus FL1 area log for a total of FL1 events residing in the window defined by the R1 gate for the same FACS run of known objects from a cell line. Events having values within gate R2 number 12124 or 2.42% of events meeting the criteria of the R1 gate. Thus, objects falling outside of gate R2 are sorted out as objects of no interest, while the remaining objects, most of which will be such as biological cells of interest, are sorted into the enriched object container.

Following specimen enrichment, cells are dehydrated in ethanol followed by suspension in xylene. The cells are then transferred to and embedded in a suitable volume of the optical medium. The optical medium is a viscous oil with matching refractive index for the optical tomography system. Once embedded, cells are injected into a disposable cartridge for imaging on the optical tomography system.

Figure 9:
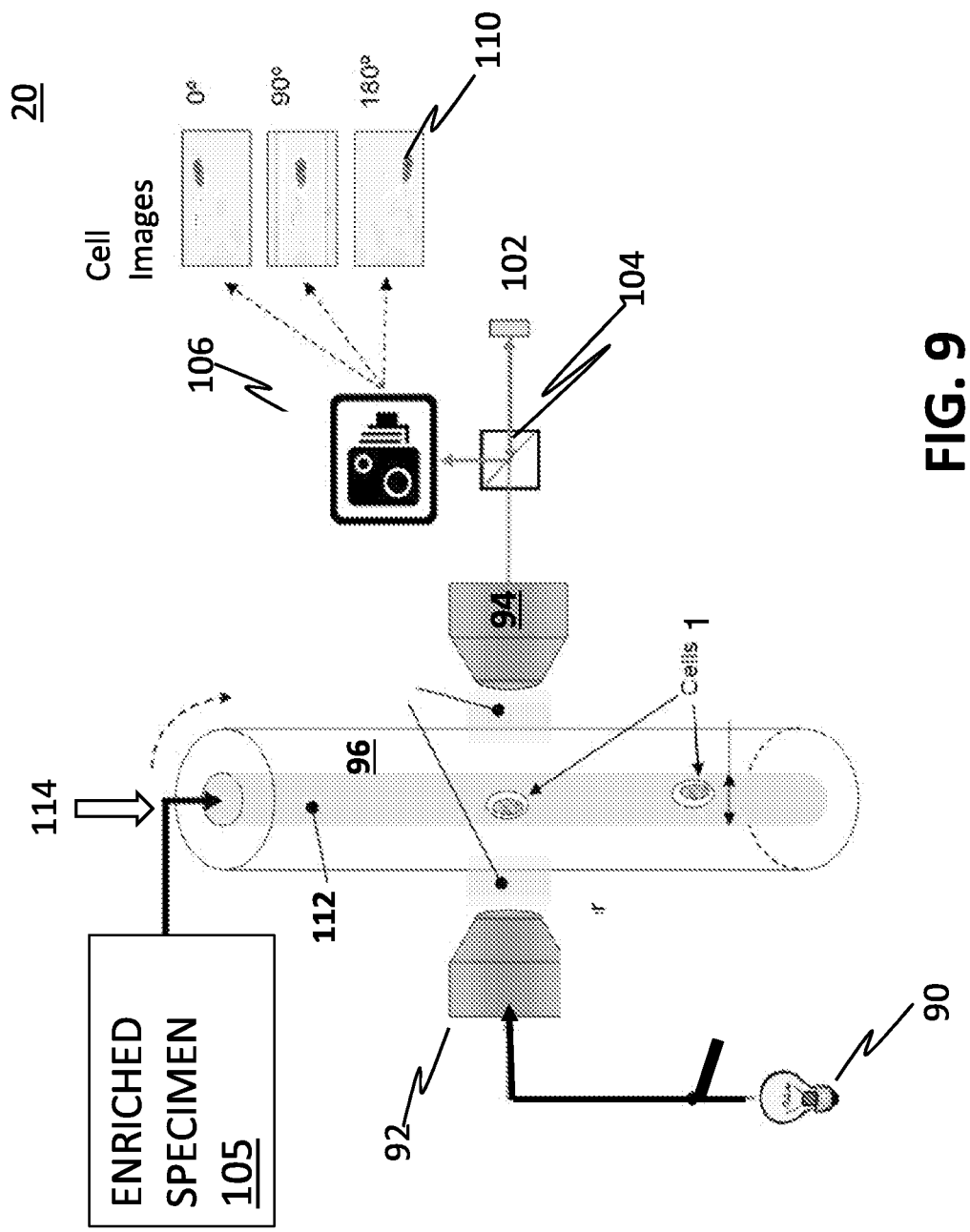
FIG. 9 schematically shows an example of basic system components of a 3D optical computed tomography imaging system used in a lung cancer test system.

Referring now to FIG. 9, basic system components of a 3D optical tomography imaging system used in a lung cancer test system are shown. The cell imaging system 20 is an automated, high-resolution 3D tomographic microscope and computing system for imaging cells in flow. Included are an illumination source 90 optically coupled to a condenser lens 92 which optically cooperates with an objective lens 94 for scanning images of objects 1 contained in a capillary tube 96. Images are obtained by scanning the volume occupied by the object by an oscillating mirror 102 and transmitted through a beam-splitter 104 to a high-speed camera 106. The high-speed camera produces a plurality of pseudo-projection images 110. A set of pseudo-projection 2D images for numerous axial tube rotation positions is produced for each object.

Although the test system is not limited to any one contrast method, in one example the lung cancer detection test specifically targets cell morphology based on the traditionally used hematoxylin stain. In the lung cancer detection test application, the optical tomography system computes 3D cell images with equal resolution in all dimensions (i.e. isotropic resolution) allowing measurements to be independent of orientation. Further, eliminating the focal plane ambiguity and view orientation dependencies typical of conventional microscopy provides information content to automatically recognize a broad spectrum of cell types, and unambiguously identify rare abnormal cells in a predominantly normal cell population. The optical tomography system output identifies about 0.5% of all cells as abnormal candidates to be verified using the CellGazer™ (VisionGate, Phoenix, AZ) workstation, an imaging software tool that allows human review of images free of focal plane and orientation ambiguity.

Optical tomography system imaging is performed on a small-volume liquid suspension. For lung cancer detection testing these cells are from the enriched epithelial cell population noted above. Because the optical tomography system can separate closely coincident objects, a narrowly focused core of single file cell flow, although a requirement in standard flow cytometry, is unnecessary.

The operation of examples of lung cancer test systems are described in the Nelson and Fauver references incorporated by reference hereinabove as well as other patents including U.S. Pat. No. 8,254,023 to Watson et al., issued Aug. 28, 2012 and entitled, "Optical Tomography System with High-Speed Scanner," which is also incorporated herein by reference. In operation stained nuclei of a biological cell 1 from an enriched specimen 105 are suspended an optical media 112 and injected into a capillary tube 96 having, for example, a 62 µm inner diameter. The capillary system has been designed to be disposable, thus eliminating the possibility of cross-contamination between specimens. Pressure 114 applied to the fluid moves objects 1 into position for imaging, before 3D data is collected as the tube rotates. A mirror 102 is actuated to sweep the plane of focus through the object, and the image is integrated by the camera to create a pseudo-projection from each single perspective. Not shown is the glass holder that interfaces the capillary tube 96 to the optical tomography system. The holder has a hole cut through the middle that is slightly larger than the outside diameter of the capillary and glass flats on either side to allow optical coupling to the objective and condenser lenses. A capillary tube that is loaded with cells embedded in transport medium is threaded through the holder. The transport media that holds the cells, the glass capillary, capillary holder, oil to interface to the lenses and the lenses themselves are made from materials of the same optical index. As a consequence, rays of light pass through the optical tomography system optics, capillary and cells without refraction while the cell may be rotated to allow capture of a set of 500 pseudo-projections is taken as the capillary rotates through 360 degrees. Because the cells are suspended in a fluid medium, they are prone to a small amount of movement while pseudo-projection images 110 are collected.

Cell images in the pseudo-projections, therefore, must be registered to a common center so that the cell features reinforce one another during the reconstruction. U.S. Pat. No. 7,835,561, entitled "Method for Image Processing and Reconstruction of Images for Optical Tomography," discloses error correction techniques for pseudo-projections. U.S. Pat. No. 7,835,561 is hereby incorporated by reference. The set of corrected pseudo-projections is processed using a filtered back-projection algorithm, similar to that in use in conventional X-ray CT, to compute the tomographic 3D cell reconstruction. Pseudo-projections images 110 taken at three angular positions: 0 g, 90 g and 180 g are shown. Illumination is provided by a light source 90 at 585 nm wavelength to optimize image contrast based on the hematoxylin absorption spectrum. In the reconstruction, 3D pixels or voxels are cubic, with a size of 70 nm in each dimension. Reconstruction volumes vary in size, as the image collection volume is cropped around the object. Typically, volumes are approximately 200-300 pixels on the side.

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by different equipment, and devices, and that various modifications, both as to the equipment details and operating procedures, may be accomplished without departing from the true spirit and scope of the present invention.

What is claimed is:

1. A method for enhancing gating performance of a cell sorter to prepare an enriched lung specimen for optical tomography cell analysis comprising:
   a) introducing a controlled specimen comprising a plurality of known target objects comprising A549 cells stained with an antibody (Ab) cocktail, the Ab cocktail comprising Pan Keratin C11 Mouse monoclonal antibodies (mAb) conjugated to Alexa 488 and Anti-Cytokeratin CK3-6H5 antibody coupled to Fluorescein Isothiocyanate (FITC), into a fluorescence-activated cell sorter (FACS) to generate 2D event data;
   b) generating a first scatterplot of the 2D event data;
   c) locating a first set of the stained known target objects in the first scatterplot, wherein the known target objects each meet or exceed a target size;
   d) constructing a first gate boundary within the first scatterplot to produce a first gate around a cluster of the known target objects;
   e) counting the known target objects within the first gate to produce a first value;
   f) comparing the first value to a first predetermined value, if the first value meets or exceeds the first predetermined value then proceeding to the next operation, otherwise, adjusting a position of the first gate boundary and repeating operations e) through f) until the first value meets or exceeds the first predetermined value;
   g) generating a second scatterplot containing a subset of the 2D event data in the first scatterplot;
   h) constructing a second gate boundary around a second set of known target objects in the second scatterplot to produce a second gate;
   i) counting the known target objects within the second gate boundary to produce a second value; and
   j) comparing the second value of target objects within the second gate to a second predetermined value, and if the percent of target objects within the second gate meets or exceeds a second predetermined value the first and second gate boundaries are stored in memory operation otherwise, the second boundary position is adjusted and operations i) and j) are repeated until the second value meets or exceeds the second predetermined value for the second gate.

2. The method of claim 1, wherein the Ab cocktail comprises fluorescent conjugate lung markers that are used to assist in depletion of inflammatory cells.

3. The method of claim 1, wherein the Ab cocktail comprises fluorescent conjugate lung markers that are used to assist in enrichment of bronchial cells.

4. The method of claim 1, further comprising:
   k) introducing a second specimen comprising a plurality of patient-derived target objects into the FACS to generate a second set of 2D event data, wherein the second specimen is a lung cell specimen;
   l) overlaying the first gate over the 2D event data and counting the patient-derived target objects within the first gate;
   m) comparing the count of patient-derived target objects to a prior iteration;
   n) if the count of target objects is optimized, the operation proceeds to count patient-derived target objects plotted within the second gate, otherwise, a position of the first gate is adjusted and operations l) through n) are repeated as necessary until optimization is achieved when the number of objects counted within the first gate reach a maximum number within a preselected tolerance;
   o) overlaying the second gate over target objects counted in the 2D event data of the first gate for counting patient-derived target objects;
   p) if not the first iteration for the second gate, then comparing the count of patient-derived target objects within the second gate to a prior iteration;
   q) if the count of target objects within the second gate is optimized, the operation proceeds to the next operation, otherwise a position of second gate is adjusted and operations o) through q) are repeated as necessary until optimization is achieved when the number of patient-derived target objects counted reach a maximum number within a preselected tolerance;
   r) storing the first and second gates in memory; and
   s) sorting patient-derived target objects bounded within both the first and second gates to produce an enriched lung cell sample.

5. The method of claim 4, wherein the specimen is a biological specimen obtained from a patient that comprises one or more of sputum, blood, a buccal swab, a venipuncture, plasma, DNA, lung organ tissue, a nasal swab, pleural effusion, and liquid biopsy samples.

6. The method of claim 4, wherein the target objects comprise biological cells that comprise one or more of lung cells, cancer cells, dysplastic cells, normal cells, epithelial cells and combinations thereof.

7. The method of claim 6, wherein the cancer cells comprise lung cancer cells.

8. The method of claim 6, wherein the epithelial cells comprise lung cells.

9. The method of claim 4, wherein the target objects comprise one or more of abnormal squamous cells, adenocarcinoma cells, bronchioloalveolar carcinoma cells, abnormal neuroendocrine cells, small cell carcinoma cells, large cell carcinoma cells, lung columnar cells, tumor cells, and neoplastic cells found in sputum.

10. The method of claim 4, further comprising:
    injecting the enriched lung specimen into a capillary tube containing fluid;
    applying pressure to the fluid moves each of the plurality of target objects into position for imaging;
    collecting image data; and
    analyzing the image data.

11. The method of claim 1, further comprising storing the first and second gates in memory and using the stored first and second gates for sorting cells from a patient specimen to provide an enriched lung cell specimen.

12. The method of claim 1, wherein the first scatterplot is a plot of the 2D event data comprising side scatter area vs. forward scatter sensor area and the second scatterplot is a plot of the 2D event data comprising side scatter area vs. fluorescence area.

13. The method of claim 1, wherein the first predetermined value is set at a minimum of at least 80%, at least 85% or at least 90% or higher of the known target objects.

14. The method of claim 1, wherein the second predetermined value is set at a minimum of at least 80%, at least 85% or at least 90% or higher of the known target objects.

* * * * *